United States Patent [19]

Seyerl

[11] Patent Number: 4,559,409

[45] Date of Patent: Dec. 17, 1985

[54] PROCESS FOR MANUFACTURING GUANYLUREA SULFAMATE

[75] Inventor: Joachim V. Seyerl, Seeon, Fed. Rep. of Germany

[73] Assignee: SKW Trostberg, Fed. Rep. of Germany

[21] Appl. No.: 551,253

[22] Filed: Nov. 14, 1983

[30] Foreign Application Priority Data

Nov. 27, 1982 [DE] Fed. Rep. of Germany ....... 3243980

[51] Int. Cl.$^4$ ............................................. C07C 127/15
[52] U.S. Cl. ........................................ 564/59; 564/32; 260/501.14
[58] Field of Search ................ 564/59, 32; 260/501.14

[56] References Cited

U.S. PATENT DOCUMENTS 2,259,563 10/1941 Hill ....................................... 564/59
2,265,942 12/1941 Hill ....................................... 564/59
3,819,518 6/1974 Endler ................................. 8/116 P Primary Examiner—Thomas A. Waltz
Assistant Examiner—R. A. Picard
Attorney, Agent, or Firm—Thomas L. Tully

[57] ABSTRACT

The present invention relates to a process for manufacturing guanylurea sulfamate, whereby dicyandiamide and sulfaminic acid are reacted in an aqueous or organic-aqueous medium at a temperature within the range 70° C.–105° C. Guanylurea sulfamate is obtained in very good yield and high purity by this process.

11 Claims, No Drawings

PROCESS FOR MANUFACTURING GUANYLUREA SULFAMATE

BACKGROUND OF THE INVENTION

The present invention relates to a process for manufacturing guanylurea sulfamate, used in industry primarily as a fire retardant for cellulose fibers.

It is known that reacting dicyandiamide with mineral acids in an aqueous medium forms the corresponding guanylurea salts according to the following equations:

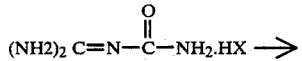

where HX=mineral acid.

Thus, in Japanese Pat. Nos. 70/40,898; 70/34,569 and 72/48,375 the manufacture of guanylurea nitrate, sulfate, and phosphate is described, whereby temperatures within the range 65° C.–100° C. are required to achieve reasonable reaction times and satisfactory yields.

Guanylurea sulfamate has not been produced in high yield by this process because of the ease with which sulfaminic acid (amidosulfonic acid) decomposes in the presence of water. Instead, the more stable salts of sulfaminic acid, such as ammonium sulfamate, were used as reactants according to U.S. Pat. No. 3,819,518. The low yield is especially disadvantageous in this reaction, since guanylurea sulfamate was produced as a mere by-product under the previously known reaction conditions, while guanidine sulfamate was formed as the primary product.

SUMMARY OF THE INVENTION

It is the object of the present invention to provide a process for manufacturing guanylurea sulfamate which overcomes the aforementioned disadvantages and makes it possible, without considerable safety-engineering expense, to produce guanylurea sulfamate in a high yield from dicyandiamide.

This object is achieved according to the present invention by conduting the reaction of dicyandiamide and sulfaminic acid in an aqueous or organic-aqueous medium at a temperature within the range of 70° C.–105° C.

Unexpectedly, it has been found that when the conditions according to the present invention are maintained, the sulfaminic acid undergoes practically no decomposition but reacts with the dicyandiamide with a high yield of more than 90% guanylurea sulfamate.

This is surprising because, as mentioned above, sulfaminic acid decomposes very rapidly at high temperatures and concentrations in the presence of water to form ammonium sulfate. (Cf. Kirk-Othmer, 1969, Vol. 19, page 243.) For example, a degree of decomposition of up to 70% can be seen under the concentration and temperature conditions according to the invention in the absence of dicyandiamide.

Moreover, consideration must also be given to the fact that any ammonium sulfate created during the decomposition of sulfaminic acid will react in known fashion with dicyandiamide to form biguanide sulfate and guanidine sulfate and will result in a considerable reduction of yield of the guanylurea sulfamate, and in the formation of these undesirable byproducts which are very difficult to separate from the desired guanylurea sulfamate.

According to the process and according to the present invention, the reaction of the dicyandiamide with sulfaminic acid is carried out in the aqueous or organic-aqueous medium at a temperature of 70° C.–105° C., preferably 70° C.–95° C. As a rule, the dicyandiamide is supplied as an aqueous solution or suspension at the corresponding reaction temperature and the sulfaminic acid, which should however not be added in excess, is then added. The sulfaminic acid can be added either as a solid, whereby however the prescribed reaction temperature must not be exceeded, or in the form of an aqueous or organic-aqueous solution, to the dicyandiamide solution or suspension.

As far as the concentration conditions are concerned, the limits are widely variable but concentrations of 10–70 wt. % preferably 40–50 wt. %, based on dicyandiamide, have proven industrially suitable. The reaction can also be performed with the stoichiometrically-necessary amount of water but appropriate means for removing heat must be provided in this instance.

The reaction can be conducted in a purely aqueous medium or in an organic-aqueous medium in which water-miscible organic solvents preferably are used.

After the reaction is complete, the guanylurea sulfamate is obtained in the usual fashion after cooling the reaction solution, by crystallization or by concentrating the solution using a water-jet vacuum, as a colorless solid in yields of more than 90% and in highly pure form, since byproducts such as guanidine or biguanidine salts are practically undetectable.

The process according to the invention therefore constitutes a simple and hence technically feasible solution for producing guanylurea sulfamate, which permits a much higher yield and purity in terms of guanylurea sulfamate by comparison with previous methods.

The examples given below are designed to explain the invention in greater detail without limiting it:

EXAMPLE 1

Sulfaminic acid (97 g) was added batchwise to a solution composed of 84 g dicyandiamide and 300 ml of water at 80° C. whereby the temperature was not permitted to exceed about 95° C. After addition was complete, the temperature was held at 95° C. for 20 minutes, after which the solution was evaporated using a water-jet vacuum. By this process 189 g (=95% of theoretical) guanylurea sulfamate was obtained.

EXAMPLE 2

Dicyandiamide (84 g) was suspended in 80 ml of water and reacted successively with 97 g sulfaminic acid at 80° C. in such manner that the temperature of 95° C. was not exceeded. The reaction mixture was agitated for another 15 minutes at 95° C. Then the solution was rapidly cooled to 0° C.–5° C., and the resultant colorless crystals were drawn off and washed with 100 ml ethanol. After drying, 181 g (91%) guanylurea sulfamate was obtained.

EXAMPLE 3

A solution of 97 g sulfaminic acid in 300 ml water was added drop by drop to a mixture of 84 g dicyandiamide, 50 ml water, and 150 ml ethanol at reflux temperature, whereby the reaction was held to the reflux temperature. After all of the sulfaminic acid has been added, the mixture was boiled for another 30 minutes with reflux after which the solvent was drawn off as in Example 1 by applying a water-jet vacuum, whereupon 187 g (94%) guanylurea sulfamate was isolated.

Variations and modifications of the present invention will be apparent to those skilled in the art within the scope of the present claims.

I claim:

1. Process for reacting equimolar amounts of dicyandiamide, sulfaminic acid and water to produce guanylurea sulfamate in high yields in excess of about 90%, comprising the steps of:
   (a) providing a solution or suspension of dicyandiamide in water or a water/organic solvent mixture;
   (b) heating said solution or suspension to a temperature within the range of 70° C. to 105° C.;
   (c) adding sulfaminic acid to said heated solution or suspension to provide a reaction medium containing at least a stoichiometrically-necessary amount of water;
   (d) controlling the temperature of said reaction medium within the range of 70° C. to 105° C. for a sufficient period of time to form guanylurea sulfamate, and
   (e) removing residual water or water/organic solvent mixture to dry said guanylurea sulfamate in a yield greater than about 90% based upon the weight of said reactants.

2. Process according to claim 1, characterized by the fact that the reaction is carried out at a temperature within the range of 70° C. to 95° C.

3. Process according to claim 1, characterized by the fact that the reaction medium comprises a 10–70%, preferably 40–50%, aqueous, or organic-aqueous solution, based on the dicyandiamide.

4. Process according to claim 2, characterized by the fact that the reaction medium comprises a 10–70%, preferably 40–50%, aqueous, or organic-aqueous solution, based on the dicyandiamide.

5. Process according to claim 1, characterized by the fact that sulfaminic acid is added as a solid to the dicyandiamide solution or suspension.

6. Process according to claim 2, characterized by the fact that sulfaminic acid is added as a solid to the dicyandiamide solution or suspension.

7. Process according to claim 3, characterized by the fact that sulfaminic acid is added as a solid to the dicyandiamide solution or suspension.

8. Process according to claim 4, characterized by the fact that sulfaminic acid is added as a solid to the dicyandiamide solution or suspension.

9. Process according to claim 1 in which only a stoichiometrically-necessary amount of water is present in the solution or suspension of the dicyandiamide, and means are employed to remove the heat of reaction and maintain the temperature within said range.

10. Process according to claim 1 in which said sulfaminic acid is added gradually to said solution or suspension of dicyandiamide.

11. Process according to claim 10 in which said sulfaminic acid is added in the form of a solution in water or water/organic solvent mixture.

* * * * *